US007053249B2

(12) United States Patent
Murthy et al.

(10) Patent No.: US 7,053,249 B2
(45) Date of Patent: May 30, 2006

(54) METAL CHELATES AND METHODS OF USING THEM FOR TIME-RESOLVED FLUORESCENCE

(75) Inventors: Yerramilli Murthy, Apex, NC (US); Robert H. Suva, Windham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 125 days.

(21) Appl. No.: 10/280,330

(22) Filed: Oct. 25, 2002

(65) Prior Publication Data

US 2004/0082768 A1 Apr. 29, 2004

(51) Int. Cl.
*C07C 49/115* (2006.01)
*G01N 33/543* (2006.01)
*G01N 33/53* (2006.01)

(52) U.S. Cl. ................... 568/326; 568/328; 568/333; 436/518; 435/7.91
(58) Field of Classification Search ............... 568/326, 568/328, 333; 436/518; 435/7.91
See application file for complete search history.

(56) References Cited

U.S. PATENT DOCUMENTS

| 4,259,313 A | 3/1981 | Frank et al. ............ 424/8 |
| 4,772,563 A | 9/1988 | Evangelista et al. ........ 436/518 |
| 5,089,423 A | 2/1992 | Diamandis et al. ......... 436/518 |
| 5,854,008 A | 12/1998 | Diamandis ............ 435/7.91 |

OTHER PUBLICATIONS

G. Romanelli et al. Efficient Deprotection of Phenol Methoxymethyl Ethers Using a Solid Acid Catalyst with Wells–Dawson Structure.□□Molecules 2001, 6, p 1006–1011.*
Afshar et al., "Dot immunoperoxidase assay using monoclonal antibody for detection of bluetongue virus antigens", Journal of Virological Methods, 31, pp. 105–112 (1991).
Archer et al., "Synthesis, Characterization, and Luminescence of Europium (III) Schiff Base Complexes,"Inorg. Chem., 37, pp. 2089–2095 (1998).
Beltyukova et al., "Terbium chelates for fluorescence immunoassays", Journal of Pharmaceutical and Biomedical Analysis, 18, pp. 267–270 (1998).
Christopoulos et al., "Ultrasensitive Time–Resolved Fluorescence Method for α–Fetoprotein", Clin. Chem., 36/8, pp. 1497–1502 (1990).
Diamandis et al., "Time–resolved fluorescence using a europium chelate of 4,7–bis, (chlorosulfophenyl)–1, 10–phenanthroline–2,9–dicarboxylic acid (BCPDA)" Journal of Immunological Methods, 112, pp. 43–52 (1988).
Diamandis, "Immunoassays with Time–Resolved Fluorescence Spectroscopy: Principles and Applications", Clin. Biochem., vol. 21, pp. 139–150 (1998).

Dickson et al., "Time–resolved detection of lanthanide luminescence for ultrasensitive bioanalytical assays", Journal of Photochemistry and Photobiology, B:Biology 27, pp. 3–19, (1995).
Gerber et al., "Immunosorbent for the Isolation of Specific Antibodies Against Mannan: Localization of Antigens in Yeast Cell Walls", Infection and Immunity, March, pp. 487–492 (1973).
Harma et al., "Europium Nanoparticles and Time–resolved Fluorescence for Ultrasensitive Detection of Prostate–specific Antigen", Clinical Chemistry 47:3, pp. 561–568 (2001).
Kricka et al., "Time–resolved fluorescence: 1996–1998", Luminescence, 14, pp. 47–61 (1999).
Oser et al., "Sensitive non–radioactive dot–blot hybridization using DNA probes labelled with chelate group substituted psoralen and quantitative detection by europium ion fluorescence", Nucleic Acid Research, vol. 16, pp. 1181–1197 (1988).
Prat et al., "Europium (III) Cryptate: A Fluorescent Label for the Detection of DNA Hybrids on Solid Support", Analytical Biochemistry, 195, pp. 283–389 (1991).
Roberts et al., "A comparison of the sensitivity and specificity of enzyme immunoassays and time–resolved fluoroimmunoassay", Journal of Immunological Methods, 143, pp. 49–56 (1991).
Scorilas et al. "Steptavidin–Polyvinylamine Conjugates Labeled with a Europium Chelate: Applications in Immunoassay, Immunohistochemistry, and Microarrays", Clinical Chemistry, 46:9, pp. 1450–1455 (2000).

(Continued)

*Primary Examiner*—Johann Richter
*Assistant Examiner*—Sikarl A. Witherspoon
(74) *Attorney, Agent, or Firm*—Fish & Richardson, P.C.

(57) ABSTRACT

β-diketone fluorescent tags are disclosed, particularly those enabling the use of excitation energy in the near visible or visible spectrum. In some cases, these tags allow the use of cost-effective excitation devices such as LED's. The compounds form fluorescent chelates (complexes) with lanthanide (III) rare earth metal ions (such as Eu3+). The fluorescent complex may be included in a latex microparticle, such as a styrene latex particle. Ideally, the complex has an absorption maximum λ equal to or greater than 360 nm, and the compound is characterized by a pKa<9.0. Kits and methods for detecting target molecules (e.g. immunoassays) are also disclosed. Such methods and kits typically use a ligand for binding to the target molecule and a labeling agent attached to the ligand. The fluorescent complexes described above are at least part of the labeling agent. Apparatus for detecting fluorescence from a sample includes an irradiating energy source that produces irradiating energy λ equal to or greater than 360 nm; a detector positioned to detect fluorescence from the sample; and a sample holder for holding the sample in position to be irradiated by the energy source. A light-emitting diode is preferably used as the irradiating energy source.

42 Claims, 8 Drawing Sheets

OTHER PUBLICATIONS

Scorilas et al., "Polyvinylamine–Streptavidin Complexes Labeled with a Europium Chelator: A Universal Detection Reagent for Solid–Phase Time Resolved Fluorometric Applications", Clinical Biochemistry, vol. 33, No. 5., pp. 345–350 (2000).

Seveus et al., "Time–Resolved Fluorescence Imaging of Europium Chelate Label in Immunohistochemistry and In Situ Hybridization", Cytometry, 13, pp. 329–338 (1992).

Soini et al., "Time–Resolved Fluorescence of Lanthanide Probes and Applications in Biotechnology", Critical Reviews in Analytical Chemistry, vol. 18, Issue 2, pp. 105–343 (1987).

Soini, "Biospecific assays with time–resolved fluorescence detection", Trends In Analytical Chemistry, vol. 9 (1990).

Steemers et. al. "New Sensitizer–Modified Calix[4] aerenes Enabling Near–UV Excitation of Complexed Luminescent Lanthanide Ions", J. Am. Chem. Soc., 117, pp. 9408–9414 (1995).

Werts et al., "Bathochromicity of Michler's ketone upon coordination with lanthanide (III) β–diketonates enables efficient sensitisation of $Eu^{3+}$ for luminescence under visible light excitation", Chem. Commun., pp. 799–800 (1999).

Werts et al., "Efficient visible light sensitisation of water–soluble near–infrared luminescent lanthanide complexes", J. Chem. Soc. 2, pp. 433–439, (2000).

Yuan et al., "A New Tetradenate β–Diketonate–Europium Chelate That Can Be Covalently Bound to Proteins for Time–Resolved Fluoroimmunoassay", Anal. Chem., 70, pp. 596–601 (1998).

* cited by examiner

CONTINUOUS vs. TIME RESOLVED FLUORESCENCE HTWM IMMUNOASSAY

| Panel# | Continuous | TR |
|---|---|---|
| 0 | 28644 | 48519 |
| 1 | 23122 | 39574 |
| 2 | 15485 | 24791 |
| 3 | 10505 | 15845 |
| 4 | 835 | 400 |
| 5 | 5877 | 8302 |
| 6 | 4114 | 5430 |
| 7 | 2324 | 2646 |
| 8 | 2274 | 2498 |
| 9 | 1588 | 1405 |
| 10 | 1257 | 1037 |
| Empty well | 760 | 30 |

Continuous (circles) vs TR(triangles) Fluorescence: HTWM Immunoassay

FIG. 5

IMMUNOASSAY FOR FELINE LEULEMIA VIRUS

1. Incubated with 100 µl of panels 1 through 6 for 30 min and washed 3 times
2. Incubated with 100 µl of biotin-FeLV-G3 for 30 min and washed 7 times
3. Incubated with 20/40 times diluted particle stock solution in 2 mg/ml BSA in PBS for 30 min and washed 7 times
4. Read Fluorescence in TR mode
5. Light source is Nichia LED of wavelength 380 nm with read time of 50 µ sec and delay time of µ sec.

| Panel# | 20 DIL' | 40 DIL' |
|--------|---------|---------|
| 1 | 97912 | 53886 |
| 2 | 47807 | 29275 |
| 3 | 31467 | 17694 |
| 4 | 3226 | 1633 |
| 5 | 24090 | 6482 |
| 6 | 20540 | 6567 |

METAL CHELATES AND METHODS OF USING THEM FOR TIME-RESOLVED FLUORESCENCE

TECHNICAL FIELD

This invention is in the general field of fluorescent complexes, particularly those having chelated metal ions; it is also in the field of synthesis and in the field of the use of chelating compounds and metal-ion complexes, for example as tags to enable detection (e.g. by instrument) in an assay.

BACKGROUND

It is often desirable to use fluorescence to detect the presence of a compound. For example, assays (such as immunoassays) can be read by detecting fluorescent energy emitted by a fluorescent tag associated with the compound being detected. Fluorescence tags are relatively easy to use, and they avoid hazards and procedures associated with radioactive tags. Useful applications for fluorescent detection include, without limitation, cell imaging, flow cytometry, immunohistochemistry, and immunoassays. Conventional fluorescent dyes include fluorescein, rhodamine, Texas Red and others.

A frequent problem in fluorescence-based assays is interference due to background fluorescence in the sample or reagents used in the assay. Because this background fluorescence often has a relatively short lifetime and low stokes shift, the use of fluorescent tags with large stokes shift or very long lifetimes (time-resolved fluorescence) allows the detection of smaller amounts of the tag in the presence of large amounts of the background. One method of time-resolved fluorescent tagging involves the use of chelated (using organic chelators) lanthanide metals. 1–6 Lanthanide chelation complexes available today require excitation with ultraviolet light (e.g., often below 340 nm 11–15), requiring complex and relatively expensive light sources, such as a nitrogen laser. Two commercial products based on lanthanide time resolved fluorescence are Perkin Elmer's DELFIA® and LANCE™ products (Perkin Elmer Bioproducts, Boston Mass.). The DELFIA® Eu-labeling reagent consists of N1-(p-isothiocyanatobenzyl)-diethylenetriamine-N1,N2,N3,N4-tetraacetic acid (DTTA) chelated with Eu3+. The DTTA group forms a stable complex with europium, and the isocyanate group reacts with a free amino group on the protein to form a stable, covalent thiourea bond. The high water solubility and stability of the chelate, in addition to the mild coupling conditions of the isothiocyanate reaction, make it possible to label antibodies with up to 10–20 Eu/IgG. The LANCE™ product is also an isocyanate (ITC) based chelating product.

The literature reports other chelates that are excitable at longer wavelengths. In some cases, these chelates exhibit relatively poor quantum yields and/or inefficient energy transfer from the chelating compound to the metal ion. For example, Eu (III) Schiff base complexes exhibit relatively low quantum yields when the absorption maximum occurs at longer wavelengths. 16 For some chelates, fluorescence is essentially limited to organic solvents, making them unattractive or impractical for biological applications. Martinus et al described a Eu chelate with Michler's ketone [4,4'-bis (N,N-dimethylamino)benzophenone] ("MK") with absorption maximum at 414 nm. Again, complex formation occurs in non-coordinating solvents, and water molecules may compete with MK for lanthanide coordination sites. 17

Steemers et al. were able to make Europium and Terbium complexes with a series of calix[4]arenes with excitations extended to at least 350 nm. The reported quantum yields are relatively low and energy transfer is relatively inefficient. It is believed that a significant fraction of the excited species are trapped by molecular oxygen resulting in quenching without contributing to luminescence. 18 Werts et al. disclose complexes of lanthanides with Fluorexon (4',5'bis[N, Nbis(carboxymethyl)aminomethyl]fluorscein) which can be excited with visible light. 19 However these chelates reportedly have relatively low quantum yields (between $1.7$–$8.9 \times 10^{-4}$) due to non-radiative deactivation.

The anion (compound 1a, below) of the aromatic 1,3-diketone, 2-naphthoyltrifluoroacetone (NTA, compound 1, below) forms a highly fluorescent Eu chelate in aqueous solvent, in the presence of the synergistic agent, tri-n-octyl-phosphene oxide (TOPO).20,21

SUMMARY

The invention features fluorescent tags exhibiting a desirable combination of one or more of the following characteristics: long lifetime, narrow band width, large stokes shift, high quantum yield, and avoidance of detrimental phenomena such as photobleaching or self-quenching. Preferably, the invention enables the use of excitation energy in the near visible or visible spectrum, allowing the use of cost-effective excitation devices such as light-emitting diodes or diode lasers, making the technology more practical for commercial use.

In general, the invention features a β-diketone compound having one of the formulas A, B or C as provided in claim 1, below. Preferably, the compound forms fluorescent chelates with lanthanide (III) rare earth metal ions (such as Eu3+), and, therefore, the invention also features complexes of the compounds with such ions. The invention also features non-fluorescent chelators, such as tri-n-octyl-phosphene oxide (TOPO) or $NH_3$, in a composition with the above fluorescent chelators. The rare earth metal ion may be included in such compositions or added to them in a later step.

In one embodiment, the fluorescent complex is incorporated on or into a microparticle, such as a styrene latex particle or on a colloidal gold particle. Preferably, the complex has an absorption maximum at λ equal to or greater than 360 nm, and the compound is characterized by a pKa<9.0 that allows the complex to be stable at physiological pH.

The complexes are particularly useful tags for detecting target molecules, and the invention features kits and methods for such detection. Such methods and kits typically use a ligand for binding to the target molecule and a labeling agent attached to the ligand. The fluorescent complexes described above are at least part of the labeling agent. The target molecule is reacted with the complex-labeled ligand, and the presence of the target is detected by irradiating with energy λ equal to or greater than 360 nm, and then detecting emission from the fluorescent complex as an indication that the target molecule is present.

Apparatus for detecting fluorescence from a sample includes an irradiating energy source that produces irradiating energy λ equal to or greater than 360 nm; a sample holder for holding the sample in position to be irradiated by the energy source, a detector positioned to detect fluorescence from the sample; and detector circuitry to allow instantaneous or time-resolved detection of the fluorescence. The invention may permit the use of a semiconductor light source such as a light-emitting diode or laser diode as the irradiating energy source.

Specifically preferred compounds according to the formula in claim 1 are those in which:

- $Ar_1$=a napthyl, anthrenyl, or phenanthrenyl group or a substituted napthyl (for example a 2' naphthyl), anthrenyl, or phenanthrenyl group;
- $Ar_2$, $Ar_3$=a substituted phenyl group, e.g., a phenyl group substituted by one or more of: —F; —$CF_3$; and —$N(CH_3)_2$;

where substitutions include $C_1$–$C_5$ alkyl, $C_1$–$C_5$ alkenyl, $C_1$–$C_5$ alkynyl groups, or substituted $C_1$–$C_5$ alkyl, $C_1$–$C_5$ alkenyl, $C_1$–$C_5$ alkynyl groups;

The details of one or more embodiments of the invention are set forth in the accompanying drawings and the description below. Other features, objects, and advantages of the invention will be apparent from the description and drawings, and from the claims.

DETAILED DESCRIPTION

Figure 1:
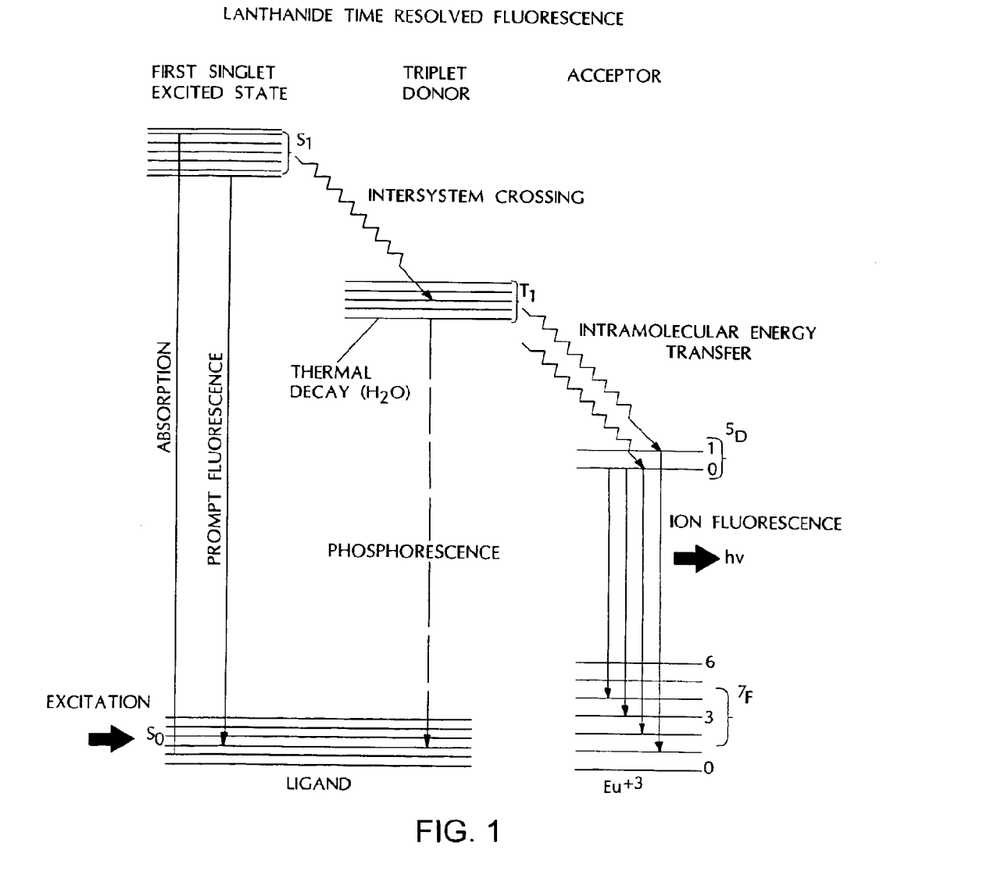
FIG. 1 is a schematic diagram of the radiative processes of an $Eu^{3+}$ chelation complex.
Figure 2:
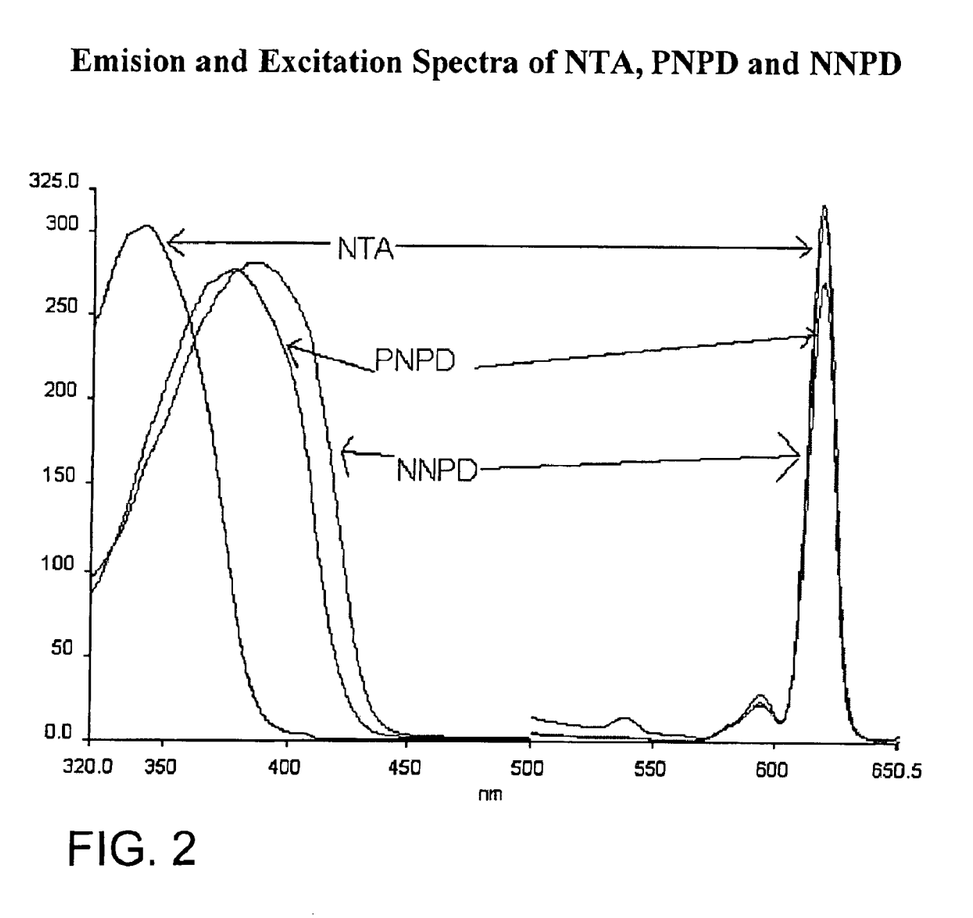
FIG. 2 is an excitation and emission spectrum of NTA, PNPD and NNPD.

Two compounds were designed in which the trifluoromethyl group in NTA (1) was replaced with a phenyl ring (phenyl-3-naphthyl-1,3-propanedione, compound 2 or "PNPD") and a naphthyl ring (1,3-di-naphthyl-1,3 propanedione, compound 3 or "NNPD"). The structures of these compounds and their corresponding enolates are shown below:

Compounds 2 and 3 were synthesized starting from 1'-acetonaphthone and their structures were characterized as described below. Fluorescent chelates of europium (III) chloride were prepared in 0.1 M borate buffer pH 9.0 with each of 2, and 3, respectively in presence of TOPO, and the excitation and emission spectra were recorded on Perkin Elmer Luminescence Spectrophotometer model LS 50 and compared with that of NTA (compound 1). Spectral results (FIG. 2) demonstrate that the peak excitation wavelengths for compounds 2 and 3 are 390 nm and 400 nm respectively; both are shifted significantly form the peak at 330 nm for compound 1 and can be excited with a semiconductor light source. The extinction and fluorescence intensity of all of the, compounds are similar. These compounds have high quantum yields coupled with stability in oxygenated solvents, suggesting efficient energy transfer from ligand to metal.

Figure 3:
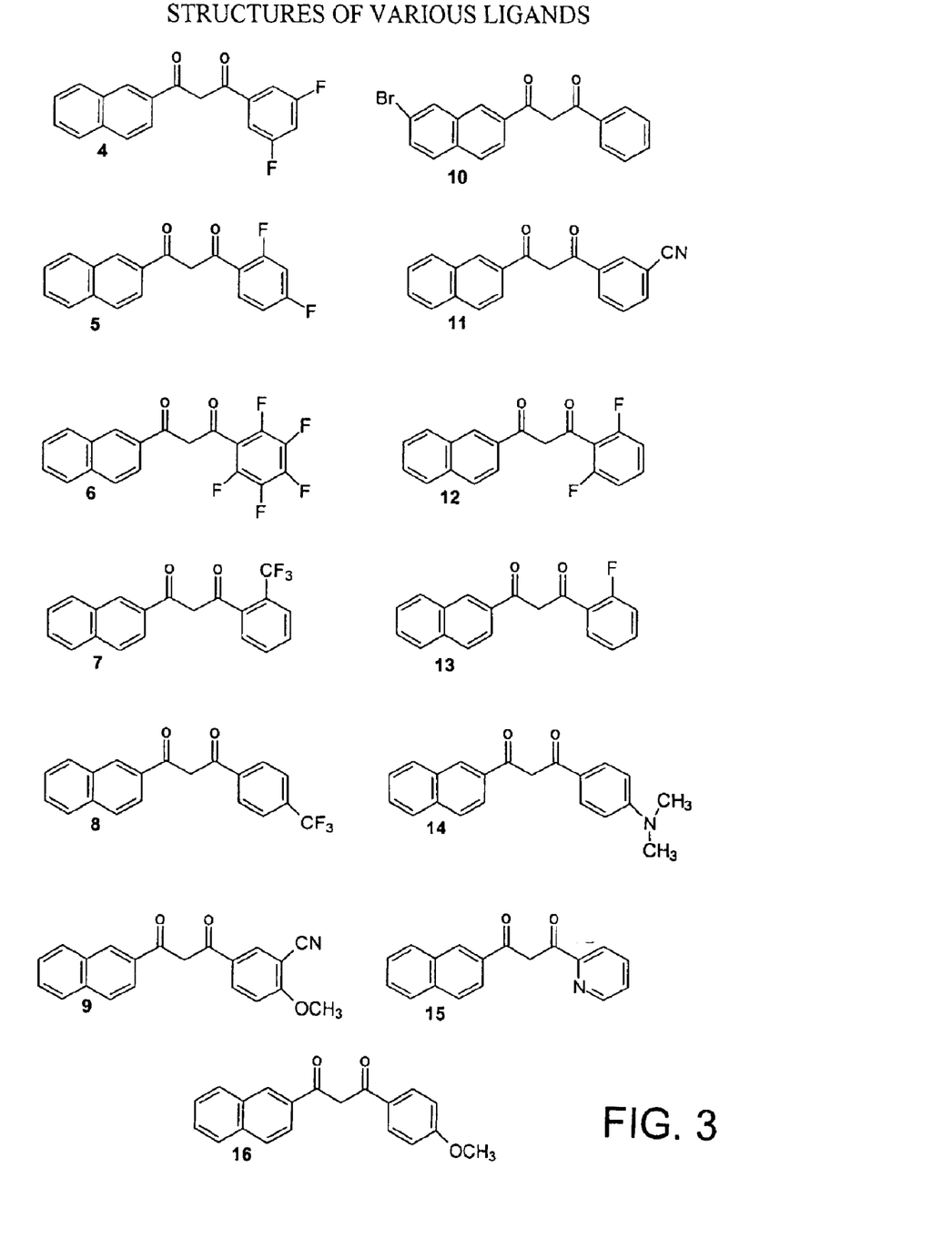
FIG. 3 shows the structures of various derivatives of compound 2.

Based on these findings, derivatives of compound 2 were prepared; their structures are depicted in FIG. 3 and their synthesis and characterization are described below.

All the compounds that are depicted in FIG. 3 can form fluorescent chelates with europium(III) chloride in presence of TOPO. Interestingly, no significant spectral shifts were observed for derivatives with different ring substituents such as fluorine, cyano, methoxy, and carboxymethyl compared to PNPD. However, significant changes in pKa of the carbonyl groups were observed. As mentioned earlier, it is necessary to form the enolate of the dicarbonyl compound for complex formation with metal to occur. In the case of unsubstituted compound 2, the pKa for the enolic carbon is ~pH 9.0 and hence it is necessary to maintain that high pH to form the complex and maintain its stability. This limits the ability to successfully load the chelate into latex particles as described below. However, the pKa of all the fluorinated derivatives is significantly lower allowing us to work with the chelates over a range of pH's. For example the pKa for compound 4 is ~4.2 which allowed us to use this compound to form a stable chelate above pH 4.5. It is usually (by not universally) desirable to stay below pH 9.0 to allow chelate stability under physiological assay conditions.

The excitation wavelength of the fluorescent chelate of N,N-dimethylamino derivative of the PNPD (compound # 14 in FIG. 3) when loaded into latex particles by the method described later, further shifted to the visible spectrum with the maximum located at ~455 nm.

Figure 4:
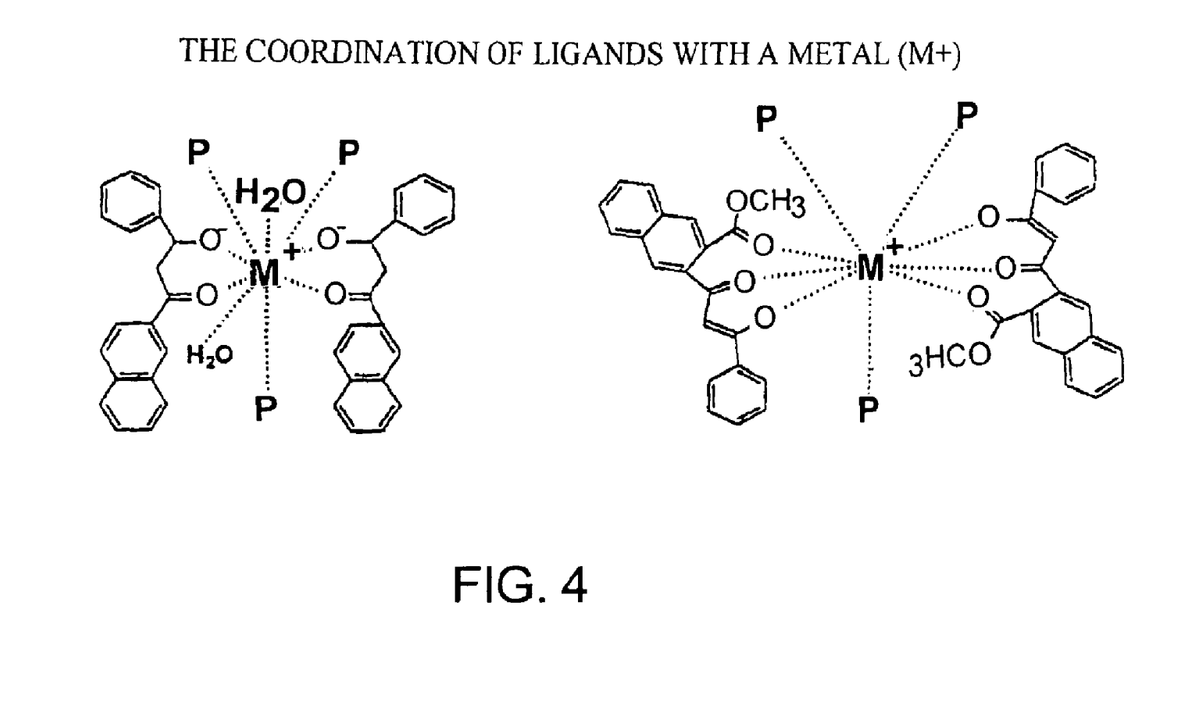
FIG. 4 diagrams the coordination of a metal (M+) with certain compounds.

Mixtures of (compound 2+TOPO) and (compound 2+europium chloride) were titrated with standard solutions of europium (III) chloride and TOPO, respectively, and fluorescence intensity was determined. Results suggested the formation of fluorescent chelate by a stoichiometric ratio of 1:3:3 of metal, ligand and TOPO. However, compounds with substitutions on phenyl ring, such as compound 4 or 8 (FIG. 3), resulted in stoichiometric ratio of 1:2:3. While we do not wish to be bound to a particular mechanism, it appears that certain of these chelates, in combination with non-fluorescent chelators such as TOPO or $NH_3$ in aqueous solution, operate as bis chelators. In other words, two fluorescent chelating molecules will complex with a single metal ion with three non-fluorescent chelators, in a 1:2:3 molar ratio. Moreover, it is possible to avoid hydration with water molecules where one of the Aryl moieties is further substituted adjacent to the diketone substituent with an additional chelating moiety. Specifically, FIG. 4 illustrates this possibility where one of the aryl moieties is substituted with:

where X=S or O, and R=O-$R_1$, or S-$R_1$, where $R_1$=$C_1$–$C_5$ alkyl, $C_1$–$C_5$ alkenyl, $C_1$–$C_5$ alkynyl groups, or substituted $C_1$–$C_5$ alkyl, $C_1$–$C_5$ alkenyl, $C_1$–$C_5$ alkynyl groups. Preferably, the further aryl substituent is —CO-O-alkyl, such as —CO-$OCH_3$. In FIG. 4, M=the metal ion, P=a non-fluorescent chelator, the organic chelating molecular formulas are shown with chelation via the oxygen molecules, and $H_2O$ indicates hydration of the complex.

Having obtained the stable chelates with desired properties, we demonstrated their potential applications in immunoassays as fluorescent probes using a simple procedure for loading the chelate into carboxy latex as described below. The new procedure was successfully used for loading a variety of carboxy latex of different size (34, 60, 104, 190, 200, 300 and 400 nm) and parking areas (7, 50, 90 Å$^2$/carboxyl group, etc), as well as plain polystyrene of different sizes, with chelates formed by different PNPD derivatives. No significant changes in the optical properties of the europium chelates were observed on loading into carboxy latex particles except that the excitation maximum was shifted to longer wavelength by 10–20 nm. Biotinylated BSA was passively adsorbed onto the chelate (which had already been loaded carboxy latex particles) followed by binding of NeutrAvidin—(Pierce Biotechnology, Rockford, Ill.) as described below.

Figure 5:
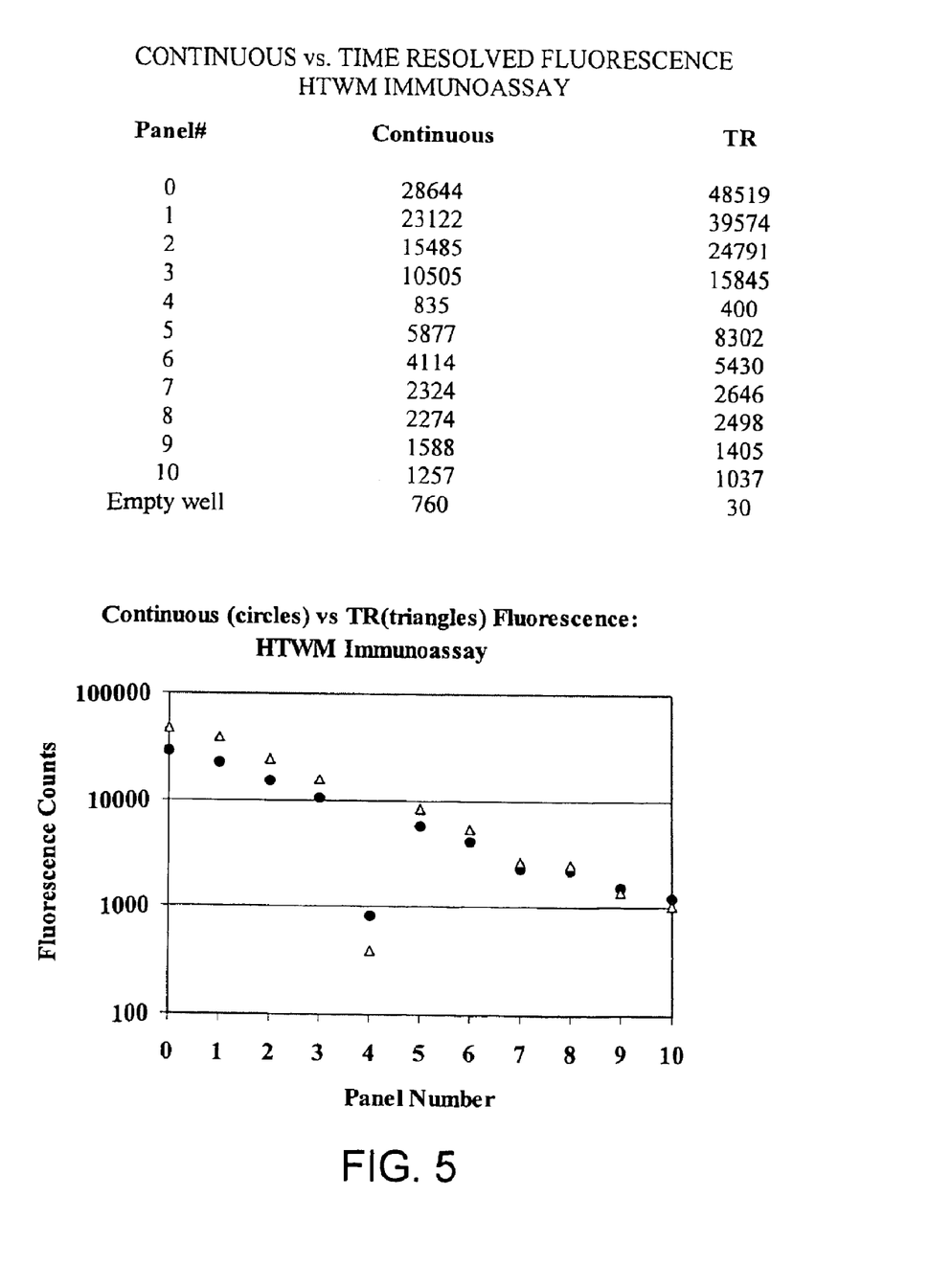
FIG. 5 compares time resolved versus continuous fluorescence as described below.

A heterogeneous sandwich immunoassay for canine heartworm (HTWM) was performed using chelate loaded carboxy latex coated with NeutrAvidin. The critical steps in the assay were as follows: Polystyrene wells were coated with rabbit anti HTWM AB followed by blocking with BSA to prevent non-specific binding. Serial dilutions of HTWM antigen in serum were incubated in these wells (the lowest concentration in panel #10 was about 0.03 ngr/ml) followed by biotinylated chicken anti HTWM AB. The wells were then washed and finally incubated with neutrAvidine-coated fluorescent carboxy latex. After thoroughly washing off the unbound particles, fluorescence was read in both continuous and time resolved mode. Results are shown in FIG. 5.

Figure 6:
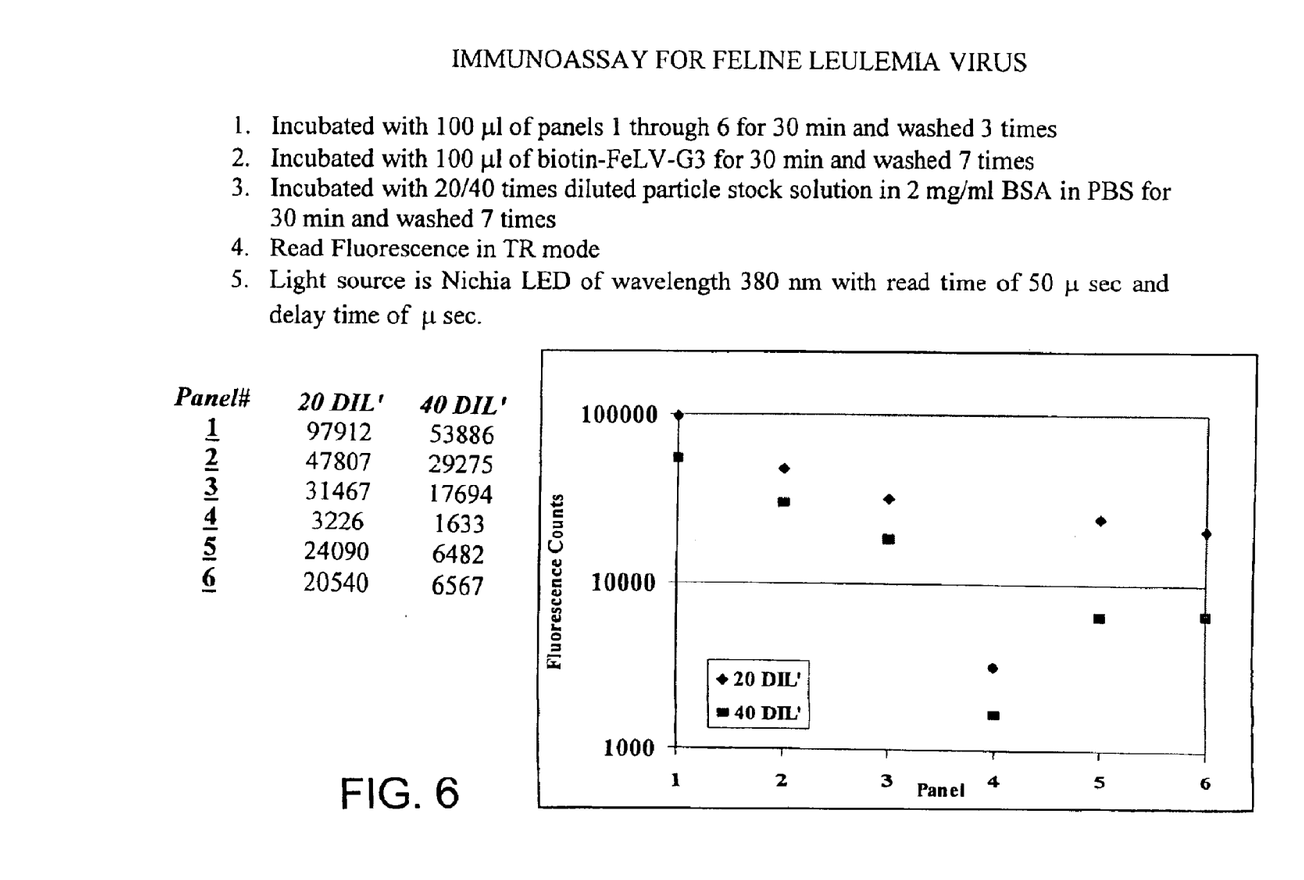
FIG. 6 depicts results from immunoassay for feline leukemia virus.

A heterogeneous sandwich immunoassay was also performed using these neutrAvidine-coated chelate-loaded carboxy latex for Feline leukemia virus (FeLV) antigen. The critical steps in the assay were as follows: The polystyrene wells were coated with monoclonal anti FeLV AB followed by blocking with BSA to prevent non-specific binding. Dilutions of an FeLV antigen panel were incubated in the wells, followed by biotinylated monoclonal anti FeLV AB. The wells were then washed and finally incubated with NeutrAvidin coated fluorescent carboxy latex. After thoroughly washing off the unbound particles, fluorescence was read in both continuous and time resolved mode. Results are shown in FIG. 6.

Figure 8:
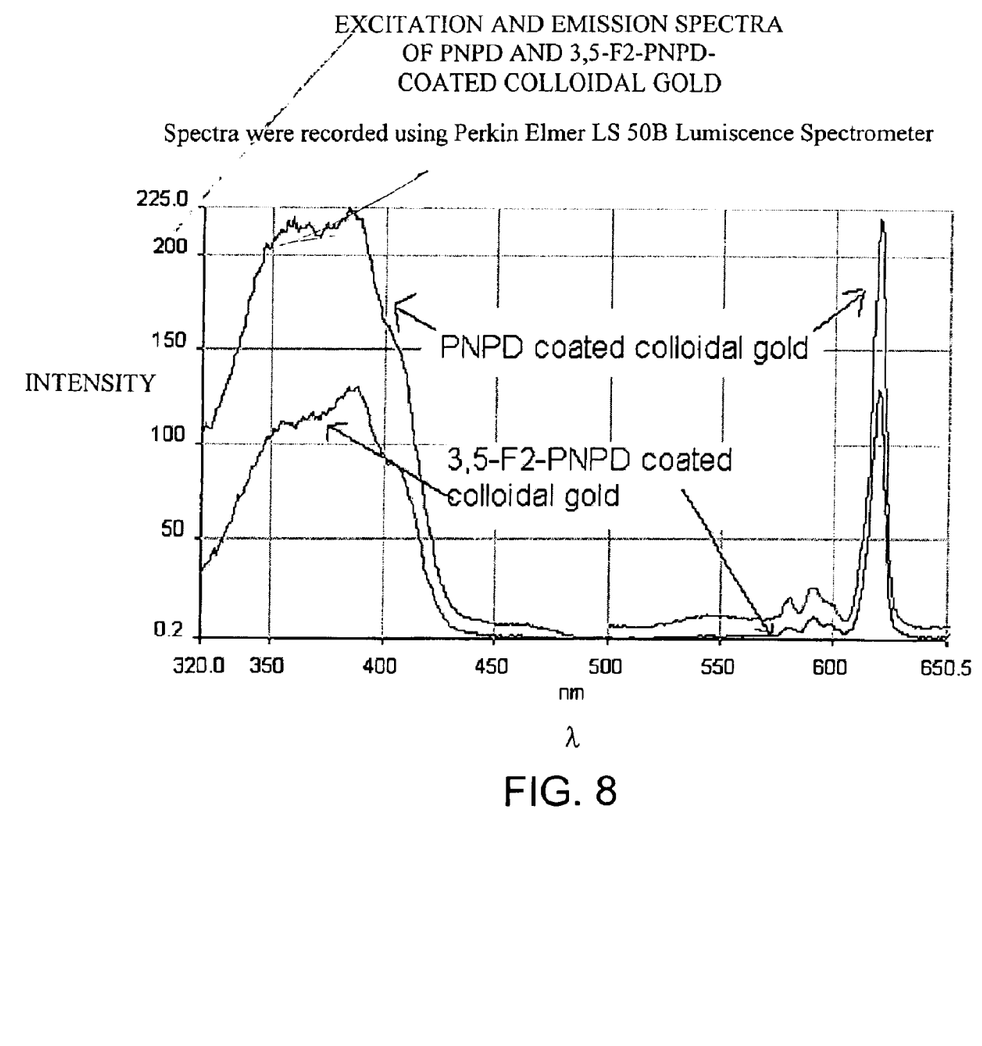
FIG. 8 is an excitation and emission spectrum of Eu-PNPD chelate coated colloidal gold.

Antibody/protein coated colloidal gold is used extensively as a probe in immunodiagnostics, histochemistry and cyctochemistry[21]. In typical immunoassays, colloidal gold provides a label for visual or qualitative detection[22]. It was reasoned that the concept of florescent colloidal gold particles would allow the gold particles to be used for both qualitative (by the visual observation of color) as well as quantitative detection (by measuring the florescence) of the targets. On these lines, a successful procedure was developed for the first time to coat the colloidal gold particles with the europium chelates. As described below, Eu chelates of PNPD and its fluorinated analogs were coated onto colloidal gold particles and the optical properties of the resulting florescent gold particles were studies as shown in FIG. 8. It was further shown that the florescent gold particles can be successfully coated with antibodies for using them as probes in immunoassays.

Figure 7:
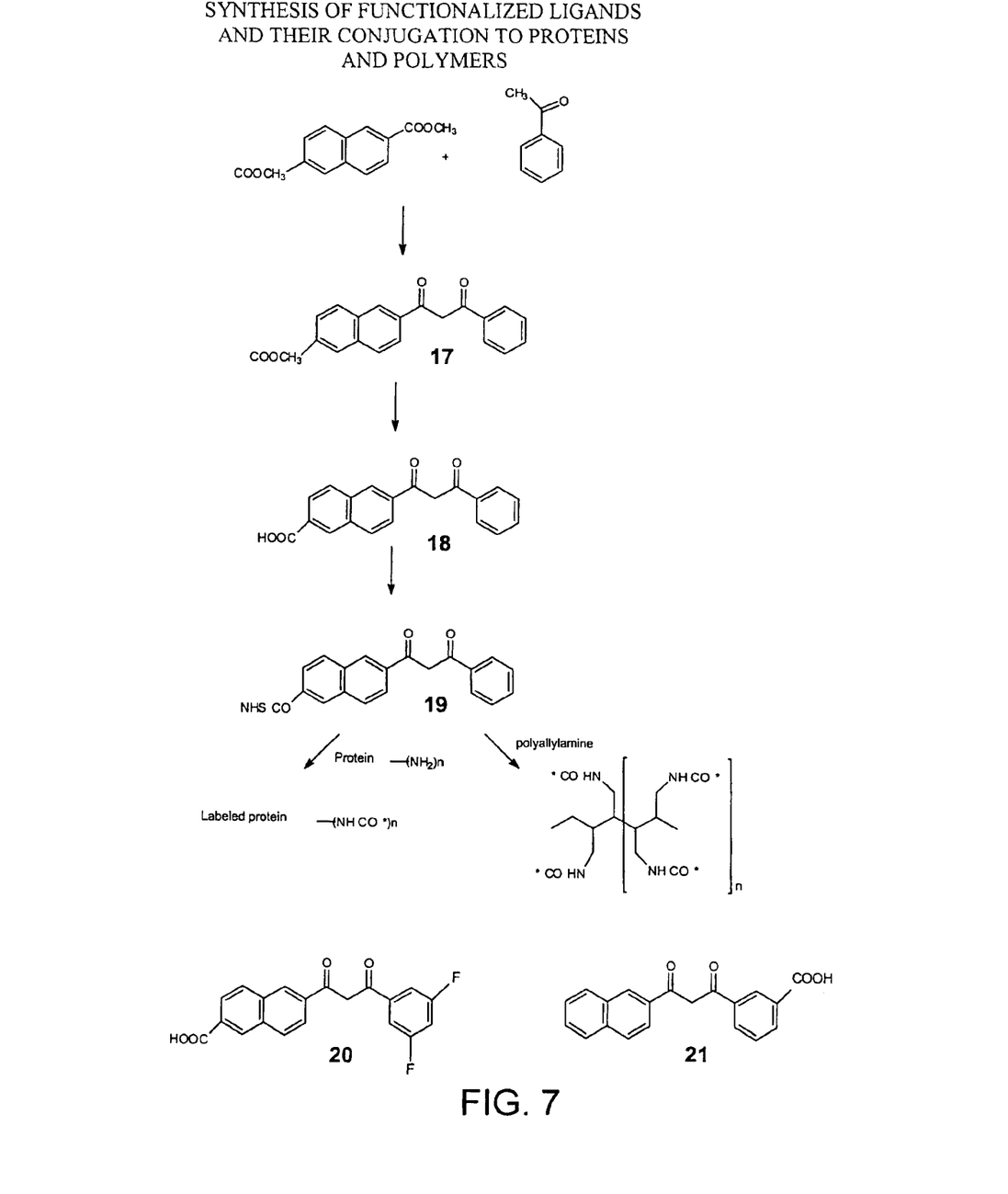
FIG. 7 is a synthetic scheme for carboxy functionalized derivatives of PNPD and their conjugation to proteins.

Three additional carboxyl functionalized derivatives of PNPD were synthesized successfully as shown in FIG. 7, to enable the direct conjugation of the new ligands to proteins. The synthesis of 1-phenyl-3(6-carbomethoxy-naphthyl)-1, 3-propanedione (17) was accomplished as described in the methods from 2,6-dimethyl-naphthlein-dicarboxylate and acetophenone. The corresponding carboxylic acid (18) was obtained by the hydrolysis of the methyl ester under sonicating conditions. The carboxylic acid derivatives (20 &21) were also synthesized using similar synthetic procedures and appropriate starting materials. It is well known that the N-hydroxysuccinimide esters of the carboxylic acid compounds reacts with the amino groups in proteins resulting in the formation of corresponding conjugates. The NHS ester of 1-phenyl-3(6-carboxy-naphthyl)-1,3-propanedione (19) was synthesized and conjugated successfully to BSA and both chicken and rabbit α HTWM Antibodies resulting in the ligand labeled proteins. Absorption spectrum of the labeled proteins have a well defined peak, characteristic of new ligands, with maxima at 360 nm suggesting successful conjugation. Labeled proteins formed fluorescent chelates when they were mixed with europium chloride and TOPO solutions. These chelate labeled antibodies allow us to run the sandwich immunoassays without using latex particles. The soluble chelate labeled antibodies shall potentially eliminate the usual diffusion associated problems that are associated with latex particles. To further enhance the sensitivity of this technology, we also successfully labeled polymers with multiple amino groups such as polyallylamine and lysine-aspartic acid polypeptides, as described, below. Further conjugation of these labeled polymers to antibodies should result in soluble protein-polymer conjugates with multiple chelate labels. The NHS ester of 1-(3, 5-$F_2$-phenyl)-3(6-carboxy-naphthyl)-1,3-propanedione was also synthesized by following similar chemistry and was used to successfully to label both proteins and polymers.

Synthesis of 1-phenyl-3-naphthyl-1,3-propanedione (2): 9.5 gr of 50% slurry of sodium amide was suspended in 100 ml of anhydrous ether in a 250 ml round bottom flask that was equipped with a magnetic stir bar and a condenser. To this suspension was added 10.2 gr of solid acetonaphthone and continued stirring for 5 min at room temperature. After 5 minutes, 8.16 gr of methylbenzoate was added in one lot as a neat liquid. At this point, the reaction flask was transferred to an oil bath and the bath temperature was raised so that the contents reflux gently in ether for 3 hours. The contents were then poured onto 300 gr of solid ice and the pH was adjusted to 7.0 with conc. HCl while stirring. The ether layer was separated and the aqueous layer was extracted with 150 ml aliquots of ether twice. Combined ether layers were dried over a bed of anhydrous sodium sulfate and concentrated on rotavapor to about 100 ml and let it sit at RT. The recrystallized solid was filtered, washed with ether and dried to obtain 10.6 gr of solid diketone.

Synthesis of 1,3-dinaphthyl-1,3-propanedione (3): 4.75 gr of 50% slurry of sodium amide was suspended in 150 ml of anhydrous ether in a 250 ml round bottom flask that was equipped with a magnetic stir bar and a condenser. To this suspension was added 5.1 gr of solid acetonaphthone and continued stirring for 5 min at room temperature. After 5 minutes, 5.58 gr of methyl-2-naphthoate was added in one lot. At this point, the reaction flask was transferred to an oil bath and the bath temperature was raised so that the contents reflux gently in ether for 3 hours. The contents were then poured onto 300 gr of solid ice. On acidification with conc. HCl, solid product fell out of solution. The solid product was filtered and recrystallized in ether/methanol mixture.

Synthesis of 1-[(3,5-$F_2$-phenyl]-3-naphthyl-1,3-propanedione (4): 2.135 gr of 50% slurry of sodium amide was suspended in 50 ml of anhydrous ether in a 100 ml round bottom flask that was equipped with a magnetic stir bar and a condenser. To this suspension was added 4.936 gr of solid acetonaphthone and continued stirring for 5 min at room temperature. After 5 minutes, 5 gr of methyl-3,5-difluorobenzoate was added in one lot. At this point, the reaction flask was transferred to an oil bath and the bath temperature was raised so that the contents reflux gently in ether for 3 hours. The contents were then poured onto 100 gr of solid ice and acidified with cont. HCl while stirring. The ether layer was separated and the aqueous layer was extracted with 100 ml aliquots of ether twice. Combined ether layers were dried over a bed of anhydrous sodium sulfate and concentrated on rotavapor to obtain a light yellow solid. The solid was dissolved in minimal volume of ether and filtered. The filtered solution was kept at 4 C to obtain crystalline product. TLC showed it as a clean single spot without any contamination.

Loading of 3,5-$F_2$-PNPD-Eu chelate into 104 nm carboxy latex: 9.3 mg of 3,5-$F_2$-PNPD in 30 ml of dioxane, 17.4 15 mg of TOPO in 45 ml of methanol and 15 ml of 1 mM Eu(II1)chloride were mixed with 100 ml of methanol. After 5 minutes, this mixture was diluted with 100 ml of DI water and put on shaker for 30 minutes to allow complete formation of the chelate. In the mean time, 2 ml of 104 nm CML latex (Seradyne, 10% solids, lot#C98 1838) was mixed with 20 µl of 6N NaOH solution and 2 ml of methanol and incubated for 30 minutes. After 30 minutes, the chelate solution and the particles were mixed together along with 80 µl of 6N NaOH and were put on a shaker for 4 hours at RT. After 4 hours, the mixture was concentrated to ~47 ml on rotavapor at 45 C under vacuum. The concentrated particle suspension was dialyzed against 6 L of 10 mM sodium chloride in DI water over 3 days, changing the dialysis buffer twice a day.

Biotinylation of BSA: 10% BSA solution (3 gr/30 ml of DIW) was filtered through 0.2 µfilter and dialyzed against 4 L of DI water. One ml of the dialyzed BSA (63.5 mg/ml) was diluted with 7 ml of 50 mM sodium phosphate buffer pH 8.0 and mixed with 0.5 ml of NHS-X-biotin (Pierce Chemical Company) solution (20 mg/ml) in anhydrous DMF and let the reaction go for 3 hrs while stirring. After 3 hrs, the reaction mixture was dialyzed against 6 L of 20 mM TRIS Ph 7.4 to get rid of the unreacted biotin.

Coating of fluorescent particles with biotin-BSA: 3 ml of particles (~0.4% solids) in 10 mM NaCl in DI water were mixed with 60~µl of 1 M TRIS Ph 7.4 and 2.5 ml of biotin/BSA (7.15 mg/ml in 20 mM TRIS Ph 7.4) in a polypropylene tube and put on rotator at 4 C overnight. Next morning, the particles were spun at 15 K rpm for 30 minutes. The pellet was resuspended in 2 ml of 20 mM TRIS Ph 7.4 and spun again. This process was repeated twice.

Finally the particles were suspended in 2 ml of 20 mM TRIS pH 7.4.

Coating of biotin-BSA coated particles with NeutrAvidine: 2 ml of above biotin-BSA coated particles in 20 mM TRIS pH 7.4 were mixed with 0.4 ml of 10 mg/ml solution of neutrAvidine in the same buffer and put on rotator at 4 C for 48 hrs. After 48 hrs, the unbound protein was removed as in the case of biotin-BSA coating procedure and the particles were finally suspended in 20 mM TRIS pH 7.4.

Determination of HTWM antigen using neutrAvidine coated fluorescent particles: The rabbit anti HTWM AB coated wells were incubated with 100 ml of HTWM antigen panels #0–10 for 30 minutes. The wells were then washed thrice with a commercially available HTWM plate wash (IDEXX Laboratories, Inc., Westbrook, Me.) followed by incubation with 5 pg/ml biotinylated chicken anti HTWM AB in HTWM conjugate diluent (IDEXX product) for 30 min. The wells were washed now 7 times followed by incubation with neutrAvidine coated fluorescent particles for an hour. After an hour, the wells were washed 7 times and read the fluorescence in time resolved as well as continuous mode. FIG. V shows the results of this assay using both continuous and time resolved fluorescence.

Synthesis of 1-phenyl-3(6-carbomethoxy-naphthyl)-1,3-propanedione: To a suspension of sodium amide (1.56 gr of 50% suspension in toluene) in anhydrous THF, was added neat acetophenone (2.88 gr) and stirred for 3 minutes at RT in a 500 ml round bottom flask equipped with a magnetic stir bar and a condenser. After 3 minutes, solid 2,6-dimethyl-naphthlein-dicarboxylate was suspended into the flask and raised the oil bath temperature to reflux THF. After 4 hrs, the reaction mixture was poured into excess ice cold water to precipitate the product. The product was filtered off and recrystallized from ethanol.

Synthesis of 1-phenyl-3(6-carboxy-naphthyl)-1,3-propanedione: One gram of 1-phenyl-3(6-carbomethoxy-naphthyl)-1,3-propanedione was suspended in 40 ml of 1N NaOH and sonicated 10 times (30 sec pulses) with a probe sonicator. The insoluble solids were filtered off and used for another cycle of sonication. The clear filtrate was acidified with conc. HCl to precipitate the carboxylic acid product. The product precipitate was dried by connecting to lyophilizer overnight. The TLC and mass spectral analysis conformed the formation of the carboxylic acid.

Synthesis of the NHS ester of 1-phenyl-3(6-carboxy-naphthyl)-1,3-propanedione: The 1-phenyl-3(6-carboxy-naphthyl)-1,3-propanedione (29.26 mg), dicyclohexyl carbodiimide (59.95 mg) and N-hydroxy-succinimide (31.77 mg) were suspended together in 1 ml of anhydrous DMF in a brown glass vial equipped with a magnetic stir bar and stirred overnight at RT. Next morning, the insoluble precipitate was filtered off and the DMF solution of the product NHS-ester was stored in a brown glass vial filled with nitrogen and used for protein conjugations without any further purification.

Conjugation of BSA with NHS ester of 1-phenyl-3(6-carboxy-naphthyl)-1,3-propanedione: Two ml of 7.82 gr/ml BSA solution in 50 mM SPB pH 8.0 was mixed with 2 aliquots of 3 μl of the above stock NHS ester solution in a glass vial equipped with a small magnetic pellet and stirred at RT for 75 min. After 75 min, the reaction mixture was passed through a size exclusion column equilibrated with 50 mM borate buffer pH 9.0 and the protein fraction was collected by following the absorption at 280 nm.

Conjugation of chicken α HTWM AB and rabbit α HTWM AB with NHS ester of 1-phenyl-3(6-carboxy-naphthyl)-1,3-propanedione: One ml of 6 mg/ml antibody solution in 50 mM SPB pH 8.0 was mixed with 6 μl of NHS ester stock solution in DMF solution in a glass vial equipped with a small magnetic pellet and stirred at RT for 75 min. After 75 min, the reaction mixture was passed through a size exclusion column equilibrated with 50 mM borate buffer pH 9.0 and the protein fraction was collected by following the absorption at 280 nm.

Conjugation of polyallylamine with NHS ester of 1-phenyl-3(6-carboxy-naphthyl)-1,3-propanedione: Two ml of 6 mg/ml solution of polyallylamine in 50 mM SPB pH 8.0 is treated with 20 μl of stock NHS-ester solution in DMF in a brown glass vial equipped with a small magnetic pellet and stirred at RT for 75 min. After 75 min, the reaction mixture was passed through size exclusion column and separated the unconjugated ligand.

Eu-PNPD Chelate coated Colloidal Gold: 10 ml of colloidal gold solution (BB International Gold Colloidal; 40 nm; CAT # EM. GC 40; Batch # 2862) was spun at 800 rpm for 15 min and the pellet was retained. The gold pellet was then dissolved in 20 ml of 0.1 M borate buffer pH 9.0 in a 50 ml glass conical flask. To this colloidal gold solution were added 400 ml each of 10% Tween 20 in DI water followed by 1 mM solution of PNPD. The mixture was the put on a shaker for 10 min. After 10 min, 400 ml each of 1 mM solutions of TOPO followed by europium chloride were added. Finally the mixture was put on shaker overnight. Next day the solution was spun at 8000 rpm for 20 min and the pellet was retained. The pellet was redissolved in 20 ml of borate buffer and spun again at 8 K rpm for 20 min. The pellet was finally dissolved in 2 ml of borate buffer to obtain a solution of fluorescent colloidal gold.

Eu-3,5-F2-PNPD chelate coated Colloidal Gold: The procedure is same as in the case of Eu-PNPD chelate except that the borate buffer was replaced with DI water.

Binding of rabbit α HTWM antibody to chelate coated colloidal gold: 119 μl of 4.5 mg/ml rabbit α HTWM solution was mixed with 881 μl of chelate coated colloidal gold solution and incubated at room temperature for 15 minutes. After 15 min, the contents were spun at 8000 rpm for 12 minutes. The pellet was dissolved in 1 ml of 0.1 M borate pH 9.0 and spun again at 8000 rpm for another 12 min. The gold pellet was finally dissolved in 1 ml of 0.1 M borate pH 9.0.

The antibody present in supernatant was measured and confirmed the binding of the protein to chelate coated gold.

A number of embodiments of the invention have been described. Nevertheless, it will be understood that various modifications may be made without departing from the spirit and scope of the invention. Further conjugation of the chelating system can be achieved. In case of anionic form (2a) of Compound 2, the conjugation is extended further by three additional double bonds of the phenyl ring, and in the case of the anionic form of compound 3a, conjugation is extended by five double bonds of the naphthyl ring. For example, a number of other potential chelating compounds may be evaluated according to the invention. In particular, as noted, compounds which exhibit absorption maxima in the visible or near visible spectrum are preferred. Aqueous solubility is also preferred. Substituent selection to produce pKa values below 9.0 are preferred, particularly when using latex particles.

Other transition metals can be used, including not only lathanide series metals but also Tr, Se, and Ru, particularly the latter.

Other immunoassays can also be performed using the fluorescing compounds of the present invention. These include, but are not limited to, assays for HIV, FIV, hepatitis, ehrlichiosis, *borrelia burgdorferi* (Lyme disease), parvovirus, leishmania, hCG, insulin, c-peptide and T4.

Accordingly, other embodiments are within the scope of the following claims.

REFERENCES

1. Prat, O., Lopez, E., Mathis, G, Anal Biochem. 1991,195, 283.
2. Oser, A., Roth, W. K., Valet, G., Nucleic Acids Res., 1988, 16, 1181.
3. Seveus, L., Vaisala, M., Syrjanen, S., Sandberg, M., Kuusisto, A., Harju, R., Salo, J., Hemmila, I., Kojola, H., Soini, E., Cytometry, 1992, 13,329.
4. Morton, R., Diamandis, E. P., Anal. Chem., 1990,62, 1841.
5. Can&A., Baily, M. P., Rocks, B. F., Analyst, 1989, 114,1908.
6. Seveus, L., Vaisala, M., Hemmila, I., Kojola, H., Roomans, G. M., Harju, R., Salo, J., Soini, E., Microsc. Res. Tech. 1994,28, 149.
7. Gudgin Dickson, E F., Pollak, A., Diamandis, E P., J. Photochem Photobiol., 1995, 27, 3–1.9.
8. Beltyukova, S V., Egorova, A V., J Pharm Biomed Anal, 1998, 18,267–70.
9. Roberts, I. M., Jones, S. L., Premier, R. R., Cox, J. C. J Immunol Methods., 199 1, 143, 49–56.
10. Soini, E., Lovgren, T., CRC Critical Reviews In Analytical Chemistry, 1987, 18, 105 154.
11. Scorilas, A., Bjartell, A., Hans, L., Moller, C., Diamandis, E. P., Chin Chem., 2000, 46, 1450–1455 and references cited therein.
12. Scorilas, A., Diamandis, E. P., CZin Biochem., 2000,33, 345–350 and references cited therein.
13. Diamandis, E. P., U.S. Pat. No. 5,854,008, Dec. 29, 1998.
14. Evangelista, R. A., Pollak, A., U.S. Pat. No. 4,772,563, Sep. 20, 1988.
15. Diamandis, E. P., Lowden, A., U.S. Pat. No. 5,089,423, Feb. 18, 1992.
16. Archer, R. D., Chen, H., Inorg. Chem., 1998,37, 2089–2095.
17. Werts, M. H. V., Duin, M. A., Hofstraat, J. W., Verhoeven, J. W., Chem. Commun., 1999,799–800.
18. Steemers, F. J., Verboom, W., Reinhoudt, D. N., Van der Tol, E. B., Verhoeven, J. W., J. Am. Chem. Sot., 1995, 117,9408–9414.

19. Werts, M. H. V., Verhoeven, J. W., Hofstraat, J. W., J. Chem. Sot., Perkin Trans., 2000, 32,433–439.
20. Hanna, H., Soukka, T., and Lovgren, T., Clinical Chem., 2001, 47:3, 561–568.
21. Gerber, H., Horisberger, M. and Bauer, H., Infect Immun, 1973, 7, 487.
22. Afshar, A., Dubuc, C., Dulac, G. C., Thomas, F. C., Nielsen, K. and Henning, D., J. Virological Methods., 1991, 31, 105–112.

What is claimed is:

1. A β-diketone containing compound having one of the following formulas A, B, or C:

Formula A

Formula B

Formula C in which
Ar$_1$ is an aromatic, heterocyclic aromatic or a substituted heterocyclic aromatic group, substituted with C$_1$–C$_5$ alkyl, C$_1$–C$_5$ alkenyl, C$_1$–C$_5$ alkynyl groups, or with substituted C$_1$–C$_5$ alkyl, C$_1$–C$_5$ alkenyl, C$_1$–C$_5$ alkynyl groups; and
Ar$_2$ and Ar$_3$ are independently selected from monocyclic aryl groups and multi-cyclic aryl groups.

2. The compound of claim 1 in which Ar$_1$=a naphthyl, anthracenyl, or phenanthrenyl group or a substituted naphthyl, anthracenyl, or phenanthrenyl group.

3. The compound of claim 1 or claim 2 in which Ar$_2$=a substituted phenyl group.

4. The compound of claim 3 in which Ar$_2$=a phenyl group substituted by one or more of: —F; —CF$_3$; —N(CH$_3$)$_2$.

5. The compound of claim 1 in which either Ar$_1$ or Ar$_2$ or both are substituted 2' to the diketone substituent with a moiety having the formula:

where X=S or O, and R=O—R$_1$ or S—R$_1$, where R$_1$=C$_1$–C$_5$ alkyl, C$_1$–C$_5$ alkenyl, C$_1$–C$_5$ alkynyl groups, or substituted C$_1$–C$_5$ alkyl, C$_1$–C$_5$ alkenyl, C$_1$–C$_5$ alkynyl groups.

6. The compound of claim 1 in which Ar$_1$ is a 2' naphthyl group.

7. A β-diketone containing compound having one of the following formulas A, B, or C:

Formula A

Formula B

Formula C in which
Ar$_1$ is an aromatic, heterocyclic aromatic or a substituted heterocyclic aromatic group; and
Ar$_2$ and Ar$_3$ are independently selected from monocyclic aryl groups and multi-cyclic aryl groups and in which either Ar$_1$ or Ar$_2$ or both are substituted 2'to the diketone substituent with a moiety having the formula:

where X=S or O, and R=O—R$_1$ or S—R$_1$, where R$_1$=C$_1$–C$_5$ alkyl, C$_1$–C$_5$ alkenyl, C$_1$–C$_5$ alkynyl groups, or substituted C$_1$–C$_5$ alkyl, C$_1$–C$_5$ alkenyl, C$_1$–C$_5$ alkynyl groups.

8. A β-diketone compound having the name 1-[(3,5 difluorophenyl]-3-naphthyl-1,3-propanedione.

9. A composition comprising the β-diketone compound of any one of claims 1–6 or claim 8 and a non-fluorescent chelator.

10. A complex of the β-diketone compound of any one of claims 1–6 or claim 8 with an ion of a lanthanide (III) rare earth metal.

11. A composition comprising the β-diketone compound and a non-fluorescent chelator, said β-diketone compound having one of the following formulas A, B, or C:

Formula A

Formula B

Formula C in which
Ar$_1$ is an aromatic, heterocyclic aromatic or a substituted heterocyclic aromatic group; and
Ar$_2$ and Ar$_3$ are independently selected from monocyclic aryl groups and multi-cyclic aryl groups.

12. A complex comprising a β-diketone compound with an ion of a lanthanide (III) rare earth metal, said said β-diketone compound having one of the following formulas A, B, or C:

in which
  $Ar_1$ is an aromatic, heterocyclic aromatic or a substituted heterocyclic aromatic group; and
  $Ar_2$ and $Ar_3$ are independently selected from monocyclic aryl groups and multi-cyclic aryl groups.

13. A composition comprising the complex of claim 10 and a non-fluorescent chelator.

14. The compound, composition or complex of any one of claims 7–12 in which substituted means substituted with $C_1$–$C_5$ alkyl, $C_1$–$C_5$ alkenyl, $C_1$–$C_5$ alkynyl groups, or substituted $C_1$–$C_5$ alkyl, $C_1$–$C_5$ alkenyl, $C_1$–$C_5$ alkynyl groups.

15. The composition of claim 13 in which the non-fluorescent chelator is tri-n-octyl-phosphene oxide (TOPO) or $NH_3$.

16. The complex of claim 10 in which the lanthanide (III) rare earth metal is $Eu^{3+}$.

17. The complex of claim 10 characterized in that the complex has an absorption maximum at S equal to or greater than 360 nm.

18. The complex of claim 10 characterized in that the β-diketone compound is characterized by a pKa<9.0.

19. The complex of claim 10 in which the complex is water soluble.

20. The complex of claim 19 in which the metal ion is $Eu^{3+}$.

21. The complex of claim 20 in which the complex comprises a non-fluorescent chelator and is a bis chelate with stoichiometry of 1:2:3 (metal ion:fluorescent compound:non-fluourescent chelator).

22. A complex of claim 10 attached to a protein or polymer.

23. A complex of claim 10 attached to an antibody or antigen.

24. A complex of claim 10, wherein the complex is covalently attached to a protein or polymer.

25. The complex of claim 24, wherein the covalent attachment is through a functional group on the β-diketone containing compound.

26. The complex of claim 25, wherein the covalently attached functional group is a carboxyl group.

27. A β-diketone compound coated on colloidal gold, in which the β-diketone compound is the compound of any one of claims 1, 7 and 8.

28. The complex of claim 12 in which $Ar_1$=a naphthyl, anthracenyl, or phenanthrenyl group or a substituted naphthyl, anthracenyl, or phenanthrenyl group.

29. The complex of claim 12 in which $Ar_2$=a substituted phenyl group.

30. The complex of claim 29 in which $Ar_2$=a phenyl group substituted by one or more of: —F; —$CF_3$; —$N(CH_3)_2$.

31. The complex of claim 12 in which either $Ar_1$ or $Ar_2$ or both are substituted 2' to the diketone substituent with a moiety having the formula:

$$O-CX-R$$

where X=S or O, and R=O—$R_1$ or S—$R_1$, where $R_1$=$C_1$–$C_5$ alkyl, $C_1$–$C_5$ alkenyl, $C_1$–$C_5$ alkynyl groups, or substituted $C_1$–$C_5$ alkyl, $C_1$–$C_5$ alkenyl, $C_1$–$C_5$ alkynyl groups.

32. The complex of claim 12 in which $Ar_1$ is a 2' naphthyl group.

33. The complex of claim 12 in which the lanthanide(III) rare earth metal is $Eu^{3+}$.

34. A latex microparticle comprising the complex of claim 12.

35. The latex microparticle of claim 34 in which the latex is a styrene latex.

36. The complex of claim 12 characterized in that the complex has an absorption maximum at S equal to or greater than 360 nm.

37. The complex of claim 12 characterized in that the multi-ketone compound is characterized by a pKa<9.0.

38. The complex of claim 12 in which the complex is water soluble.

39. The complex of claim 38 in which the metal ion is $Eu^{3+}$.

40. The complex of claim 39 in which the complex comprises a non-fluorescent chelator and is a bis chelate with stoichiometry of 1:2:3 (metal ion:fluorescent compound:non-fluourescent chelator).

41. A composition coated on colloidal gold, in which the composition is the composition of claim 25.

42. A β-diketone complex coated on colloidal gold, in which the β-diketone complex is the complex of claim 26.

* * * * *

UNITED STATES PATENT AND TRADEMARK OFFICE
CERTIFICATE OF CORRECTION

| | | |
|---|---|---|
| PATENT NO. | : 7,053,249 B2 | Page 1 of 1 |
| APPLICATION NO. | : 10/280330 | |
| DATED | : May 30, 2006 | |
| INVENTOR(S) | : Yerramilli Murthy and Robert H. Suva | |

It is certified that error appears in the above-identified patent and that said Letters Patent is hereby corrected as shown below:

Column 12, line 23, "2'to" should be --2 to --.

Column 13, line 2, delete the second occurrence of "said".

Column 14, line 33, "claims 7-12" should be -- claims 7, 11-12 --.

Column 14, line 51, "claim 25" should be -- claim 11 --.

Column 14, line 53, "claim 26" should be -- claim 12 --.

Signed and Sealed this

Eighteenth Day of December, 2007

JON W. DUDAS
*Director of the United States Patent and Trademark Office*